US006602231B1

United States Patent
Mariea

(10) Patent No.: US 6,602,231 B1
(45) Date of Patent: Aug. 5, 2003

(54) SPECIMEN COLLECTION ASSEMBLY INCLUDING A CUP AND TELESCOPING HANDLE

(76) Inventor: Dianne C. Mariea, 457 Sunset Blvd., Toledo, OH (US) 43612

( * ) Notice: Subject to any disclaimer, the term of this patent is extended or adjusted under 35 U.S.C. 154(b) by 35 days.

(21) Appl. No.: 09/953,044

(22) Filed: Sep. 14, 2001

(51) Int. Cl.⁷ .................................................. A61M 1/00
(52) U.S. Cl. ..................................................... 604/317
(58) Field of Search ............................... 604/317, 356; 220/757, 762–764

(56) References Cited

U.S. PATENT DOCUMENTS

| | | | | |
|---|---|---|---|---|
| 403,656 A | * | 5/1889 | Gerstle | 220/763 |
| 3,625,654 A | | 12/1971 | Van Duyne | |
| 3,812,997 A | * | 5/1974 | McNally | 220/529 |
| 3,937,509 A | * | 2/1976 | Hufnagel | 294/1.4 |
| 4,042,269 A | * | 8/1977 | Skermetta | 294/1.5 |
| 4,144,461 A | * | 3/1979 | Glasser et al. | 250/506.1 |
| 4,244,920 A | | 1/1981 | Manschot et al. | |
| D258,311 S | | 2/1981 | Peterson | |
| 4,788,862 A | | 12/1988 | Fuller | |
| 4,866,809 A | * | 9/1989 | Pelletier | 15/167.1 |
| 5,033,520 A | * | 7/1991 | Kuehmichel | 141/231 |
| 5,147,342 A | | 9/1992 | Kane et al. | |
| 5,242,093 A | * | 9/1993 | Worrell et al. | 222/470 |
| 5,370,409 A | * | 12/1994 | Latouche | 280/47.26 |
| 5,492,220 A | | 2/1996 | Estay | |
| 5,634,569 A | * | 6/1997 | DeCoster | 220/735 |
| 5,845,807 A | * | 12/1998 | De Villiers | 220/703 |
| 6,073,944 A | * | 6/2000 | Moore | 280/47.26 |
| 6,390,431 B1 | * | 5/2002 | Ott | 248/311.2 |

* cited by examiner

Primary Examiner—Weilun Lo
Assistant Examiner—Michael G Bogart

(57) ABSTRACT

A specimen collection assembly for providing convenience for the user when collecting one's specimen. The specimen collection assembly includes a cup member having side and bottom walls, and also having an open top and a spout portion for dispensing specimen from the cup member; and also includes a lid member being removably attached upon the cup member; and further includes a telescopic handle member having a plurality of tubular members and being attached to the cup member.

11 Claims, 1 Drawing Sheet

SPECIMEN COLLECTION ASSEMBLY INCLUDING A CUP AND TELESCOPING HANDLE

BACKGROUND OF THE INVENTION

1. Field of the Invention

The present invention relates to specimen collection devices and more particularly pertains to a new specimen collection assembly for providing convenience for the user when collecting one's specimen.

2. Description of the Prior Art

The use of specimen collection devices is known in the prior art. More specifically, specimen collection devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,244,920; 4,788,862; 3,625,654; 5,492,220; 5,147,342; and U.S. Pat. No. Des. 258,311.

While these devices fulfill their respective, particular objectives and requirements, the aforementioned patents do not disclose a new specimen collection assembly. The inventive device includes a cup member having side and bottom walls, and also having an open top and a spout portion for dispensing specimen from the cup member; and also includes a lid member being removably attached upon the cup member; and further includes a telescopic handle member having a plurality of tubular members and being attached to the cup member.

In these respects, the specimen collection assembly according to the present invention substantially departs from the conventional concepts and designs of the prior art, and in so doing provides an apparatus primarily developed for the purpose of providing convenience for the user when collecting one's specimen.

SUMMARY OF THE INVENTION

In view of the foregoing disadvantages inherent in the known types of specimen collection devices now present in the prior art, the present invention provides a new specimen collection assembly construction wherein the same can be utilized for providing convenience for the user when collecting one's specimen.

The general purpose of the present invention, which will be described subsequently in greater detail, is to provide a new specimen collection assembly which has many of the advantages of the specimen collection devices mentioned heretofore and many novel features that result in a new specimen collection assembly which is not anticipated, rendered obvious, suggested, or even implied by any of the prior art specimen collection devices, either alone or in any combination thereof.

To attain this, the present invention generally comprises a cup member having side and bottom walls, and also having an open top and a spout portion for dispensing specimen from the cup member; and also includes a lid member being removably attached upon the cup member; and further includes a telescopic handle member having a plurality of tubular members and being attached to the cup member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new specimen collection assembly which has many of the advantages of the specimen collection devices mentioned heretofore and many novel features that result in a new specimen collection assembly which is not anticipated, rendered obvious, suggested, or even implied by any of the prior art specimen collection devices, either alone or in any combination thereof.

It is another object of the present invention to provide a new specimen collection assembly which may be easily and efficiently manufactured and marketed.

It is a further object of the present invention to provide a new specimen collection assembly which is of a durable and reliable construction.

An even further object of the present invention is to provide a new specimen collection assembly which is susceptible of a low cost of manufacture with regard to both materials and labor, and which accordingly is then susceptible of low prices of sale to the consuming public, thereby making such specimen collection assembly economically available to the buying public.

Still yet another object of the present invention is to provide a new specimen collection assembly which provides in the apparatuses and methods of the prior art some of the advantages thereof, while simultaneously overcoming some of the disadvantages normally associated therewith.

Still another object of the present invention is to provide a new specimen collection assembly for providing convenience for the user when collecting one's specimen.

Yet another object of the present invention is to provide a new specimen collection assembly which includes a cup member having side and bottom walls, and also having an open top and a spout portion for dispensing specimen from the cup member; and also includes a lid member being removably attached upon the cup member; and further includes a telescopic handle member having a plurality of tubular members and being attached to the cup member.

Still yet another object of the present invention is to provide a new specimen collection assembly that is easy and convenient to use.

Even still another object of the present invention is to provide a new specimen collection assembly that prevents the user from getting one's specimen on one's hands.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
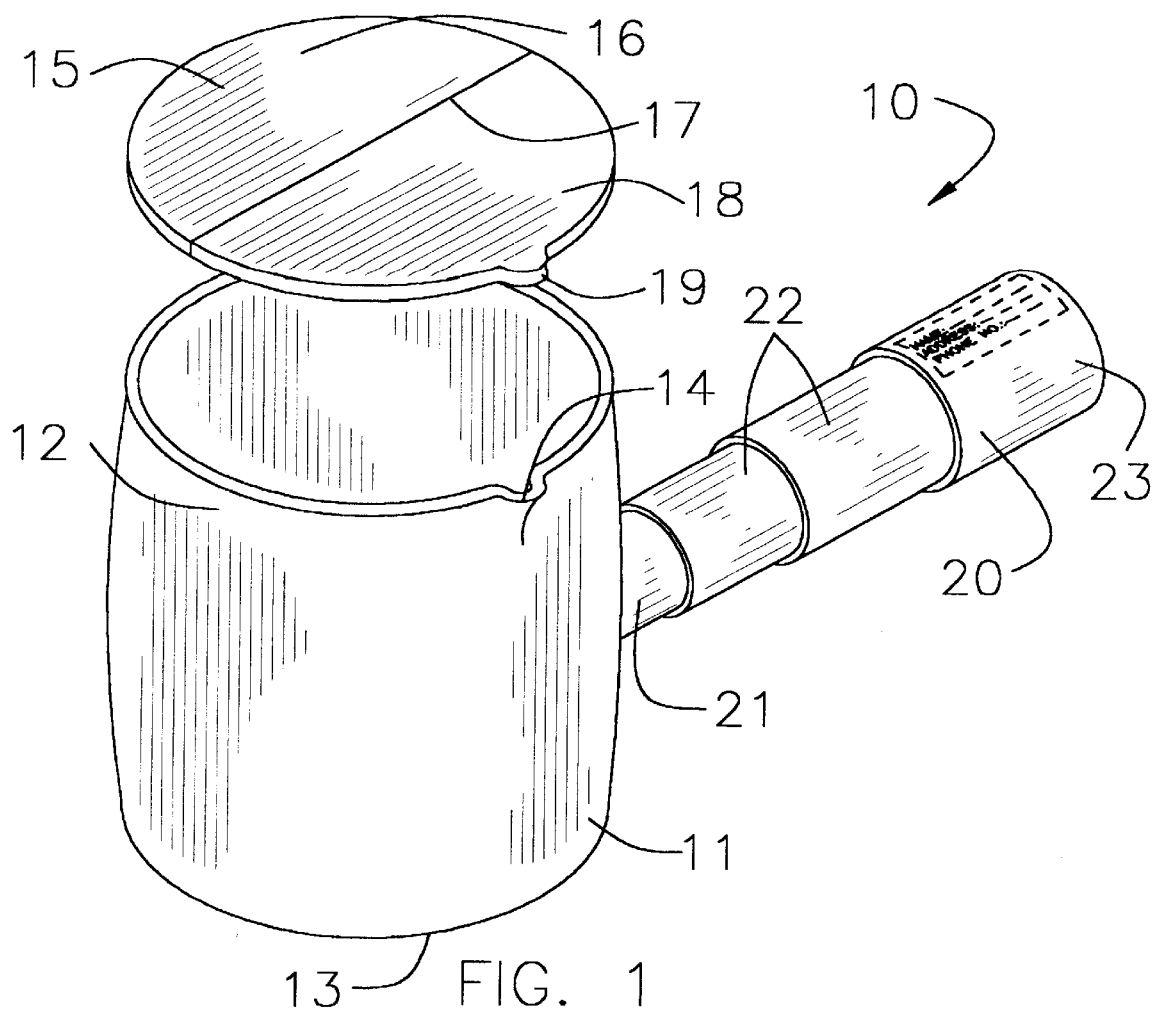
FIG. 1 is a perspective view of a new specimen collection assembly according to the present invention.
Figure 2:
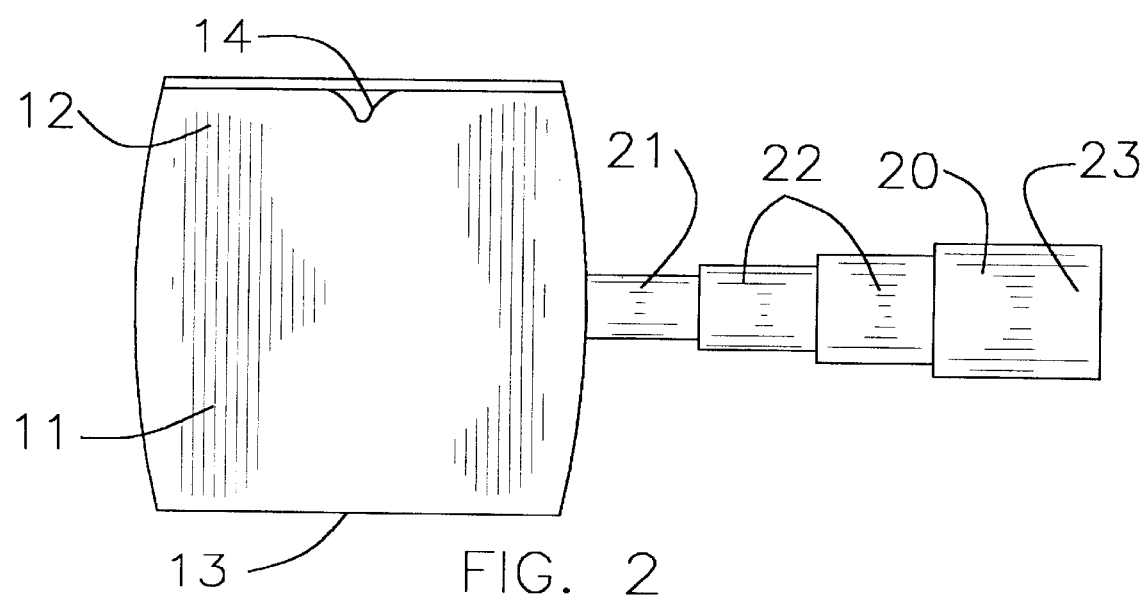
FIG. 2 is a side elevational view of the present invention.

With reference now to the drawings, and in particular to FIGS. 1 through 2 thereof, a new specimen collection assembly embodying the principles and concepts of the present invention and generally designated by the reference numeral 10 will be described.

As best illustrated in FIGS. 1 through 2, the specimen collection assembly 10 generally comprises a cup member 11 having side and bottom walls 12,13, and also having an open top and a spout portion 14 for dispensing specimen from the cup member 11. The spout portion 14 is integrally formed in a top edge of the side wall 12 and projects outwardly of the side wall 12. A lid member 15 is removably attached upon the cup member 11. The lid member 15 includes a main wall 16 having a curved edge and a straight edge 17, and also includes a second wall 18 being hingedly attached along the straight edge 17 of the main wall 16 and having a projecting portion 19 extending outwardly from an edge thereof and being removably disposed upon the spout portion 14 of the cup member 11 for the closing thereof.

A telescopic handle member 20 has a plurality of tubular members 21–23 and is conventionally attached to the cup member 11. The tubular members 21–23 includes a first tubular member 21 which is conventionally attached to an exterior of the side wall 14 of the cup member 11, and also includes a plurality of intermediate tubular members 22 being telescopingly connected to the first tubular member 21, and further includes an end tubular member 23 which is telescopingly connected to the intermediate tubular member 22 for adjustably lengthening and shortening the telescopic handle member 20 as desired by the user.

In use, the user lockingly extends the tubular members 21–23 to the desired extension and places the cup member 11 between one's legs by holding onto the end tubular member 23 of the handle member 20 to collect one's specimen.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A specimen collection assembly comprising:
   a cup member having side and bottom walls, and also having an open top and a spout portion for dispensing specimen from said cup member;
   a lid member being removably attached upon said cup member;
   a telescopic handle member having a plurality of tubular members and being attached to said cup member; and
   a label coupled to said telescopic handle for facilitating identification of said specimen.

2. A specimen collection assembly as described in claim 1, wherein said spout portion is integrally formed in a top edge of said side wall and projects outwardly of said side wall.

3. A specimen collection assembly as described in claim 1, wherein said lid member includes a main wall having a curved edge and a straight edge, and also includes a second wall being hingedly attached along said straight edge of said main wall and having a projecting portion extending outwardly from an edge thereof and being removably disposed upon said spout portion of said cup member for the closing thereof.

4. A specimen collection assembly as described in claim 1, wherein said tubular members includes a first tubular member which is attached to an exterior of said side wall of said cup member, and also includes a plurality of intermediate tubular members telescopingly connected to said first tubular member, and further includes an end tubular member which is telescopingly connected to said intermediate tubular member for adjustably lengthening and shortening said telescopic handle member.

5. A specimen collection assembly comprising:
   a cup member having side and bottom walls, and also having an open top and a spout portion for dispensing specimen from said cup member, said spout portion being integrally formed in a top edge of said side wall and projecting outwardly of said side wall;
   a lid member being removably attached upon said cup member, said lid member including a main wall having a curved edge and a straight edge, and also including a second wall being hingedly attached along said straight edge of said main wall and having a projecting portion extending outwardly from an edge thereof and being removably disposed upon said spout portion of said cup member for the closing thereof;

a telescopic handle member having a plurality of tubular members and being attached to said cup member, said tubular members including a first tubular member which is attached to an exterior of said side wall of said cup member, and also including a plurality of intermediate tubular members telescopingly connected to said first tubular member, and further including an end tubular member which is telescopingly connected to said intermediate tubular member for adjustably lengthening and shortening said telescopic handle member;

said end tubular member being visible when said telescopic handle is in a retracted position;

a label coupled to said end tubular member for facilitating identification of said specimen; and wherein a top portion of said side wall of said cup member is curved such that said top portion tapers from a middle of said side wall to a top of said side wall for facilitating comfortable positioning of said cup member between legs of the user when collecting the specimen.

6. The specimen collection assembly of claim 1, wherein said telescopic handle includes an end tubular member, said end tubular member being visible when said telescopic handle is in a retracted position; and said label being positioned on said end tubular member whereby said label remains visible when said telescopic handle is in said retracted position.

7. A specimen collection assembly comprising:

a cup member having side and bottom walls, and also having an open top and a spout portion for dispensing specimen from said cup member;

a lid member being removably attached upon said cup member;

a telescopic handle member having a plurality of tubular members and being attached to said cup member; and wherein a top portion of said side wall of said cup member is curved such that said top portion tapers from a middle of said side wall to a top of said side wall for facilitating comfortable positioning of said cup member between legs of the user when collecting the specimen.

8. The specimen collection assembly of claim 7, wherein said telescopic handle includes an end tubular member, said end tubular member being visible when said telescopic handle is in a retracted position; and said label being positioned on said end tubular member whereby said label remains visible when said telescopic handle is in said retracted position.

9. A specimen collection assembly as described in claim 7, wherein said spout portion is integrally formed in a top edge of said side wall and projects outwardly of said side wall.

10. A specimen collection assembly as described in claim 7, wherein said lid member includes a main wall having a curved edge and a straight edge, and also includes a second wall being hingedly attached along said straight edge of said main wall and having a projecting portion extending outwardly from an edge thereof and being removably disposed upon said spout portion of said cup member for the closing thereof.

11. A specimen collection assembly as described in claim 7, wherein said tubular members includes a first tubular member which is attached to an exterior of said side wall of said cup member, and also includes a plurality of intermediate tubular members telescopingly connected to said first tubular member, and further includes an end tubular member which is telescopingly connected to said intermediate tubular member for adjustably lengthening and shortening said telescopic handle member.

* * * * *